US00PP15492P2

(12) United States Plant Patent
Oya

(10) Patent No.: US PP15,492 P2
(45) Date of Patent: Jan. 25, 2005

(54) ***PETUNIA* PLANT NAMED 'BLUETTE WHITE'**

(50) Latin Name: *Petunia×hybrida*
Varietal Denomination: Bluette White

(75) Inventor: Horotaka Oya, Sunto-gun (JP)

(73) Assignee: Dai-Ichi Seed Co., Ltd., Tokyo (JP)

( * ) Notice: Subject to any disclaimer, the term of this patent is extended or adjusted under 35 U.S.C. 154(b) by 0 days.

(21) Appl. No.: 10/820,507

(22) Filed: Apr. 7, 2004

(51) Int. Cl.[7] ..... A01H 5/00
(52) U.S. Cl. ..... Plt./356
(58) Field of Search ..... Plt./356

*Primary Examiner*—Kent Bell
(74) *Attorney, Agent, or Firm*—C. A. Whealy

(57) ABSTRACT

A new and distinct cultivar of *Petunia* plant named 'Bluette White', characterized by its low spreading and trailing plant habit; vigorous growth habit; freely branching habit; numerous small white-colored flowers; and good garden performance.

1 Drawing Sheet

Botanical classification: *Petunia×hybrida* cultivar Bluette White.

BACKGROUND OF THE INVENTION

The present Invention relates to a new and distinct cultivar of *Petunia* plant, botanically known as *Petunia×hybrida,* and hereinafter referred to by the cultivar name Bluette White.

The new *Petunia* is a product of a planned breeding program conducted by the Inventor in Shizuoka, Japan. The objective of the breeding program is to create vigorous freely branching *Petunias* with numerous small flowers, attractive flower coloration, and low and high temperature tolerance.

The new *Petunia* originated from a cross-pollination made by the Inventor in 1998 of the *Petunia×hybrida* cultivar Bluette Purple, not patented, as the female, or seed parent, with an unnamed proprietary *Petunia×hybrida* seedling selection, not patented, as the male, or pollen parent. The new *Petunia* was selected as a single plant from the resulting progeny of the cross-pollination by the Inventor in a controlled environment in Shizuoka, Japan.

Asexual reproduction of the new cultivar by vegetative cuttings taken in Shizuoka, Japan since July, 1999, has shown that the unique features of this new *Petunia* are stable and reproduced true to type in successive generations.

SUMMARY OF THE INVENTION

Plants of the cultivar Bluette White have not been observed under all possible environmental conditions. The phenotype may vary somewhat with variations in environment such as temperature and light intensity without, however, any variance in genotype.

The following traits have been repeatedly observed and are determined to be the unique characteristics of 'Bluette White'. These characteristics in combination distinguish 'Bluette White' as a new and distinct cultivar:

1. Low spreading and trailing plant habit.
2. Vigorous growth habit.
3. Freely branching habit.
4. Numerous small white-colored flowers.
5. Good garden performance.

Plants of the new *Petunia* differ from plants of the female parent, the cultivar Bluette Purple, primarily in flower color as plants of the cultivar Bluette Purple have purple-colored flowers. Compared to plants of the male parent selection, plants of the new *Petunia* are more vigorous and have a more trailing and freely branching plant habit.

Plants of the new *Petunia* can be compared to plants of the cultivar Surfinia White, not patented. In side-by-side comparisons conducted in Shizuoka, Japan, plants of the new *Petunia* differed from plants of the cultivar Surfinia White in the following characteristics:

1. Plants of the new *Petunia* had thinner stems than plants of the cultivar Surfinia White.
2. Plants of the new *Petunia* had smaller leaves than plants of the cultivar Surfinia White.
3. Plants of the new *Petunia* had smaller flowers than plants of the cultivar Surfinia White.
4. Plants of the new *Petunia* had shorter peduncles than plants of the cultivar Surfinia White.

Plants of the new *Petunia* can also be compared to plants of the cultivar White Wave, not patented. In side-by-side comparisons conducted in Shizuoka, Japan, plants of the new *Petunia* differed from plants of the cultivar White Wave in the following characteristics:

1. Plant habit of plants of the new *Petunia* was not as trailing as plant habit of plants of the cultivar White Wave.
2. Plants of the new *Petunia* had smaller leaves than plants of the cultivar White Wave.
3. Plants of the new *Petunia* had smaller flowers than plants of the cultivar White Wave.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the colors of the new *Petunia.*

The photograph at the bottom of the sheet comprises a side perspective view of a typical flowering plant of 'Bluette White' grown in a container.

The photograph at the top of the sheet comprises close-up views of typical leaves and flowers of 'Bluette White'.

DETAILED BOTANICAL DESCRIPTION

The aforementioned photographs and following observations and measurements describe plants grown in Lompoc, Calif., under commercial practice during the winter in a polycarbonate-covered greenhouse with day temperatures ranging from 21 to 24° C., night temperatures ranging from 15 to 18° C., and light levels ranging from 5,000 to 9,000 foot candles. Plants were grown for about 14 weeks with one plant per 10-cm container. Plants were pinched once about three weeks after planting. In the following description, color references are made to The Royal Horticultural Society Colour Chart, 1995 Edition, except where general terms of ordinary dictionary significance are used.

Botanical classification: *Petunia×hybrida* cultivar Bluette White.

Parentage:

*Female parent.*—*Petunia×hybrida* cultivar Bluette Purple, not patented.

*Male parent.*—Unnamed proprietary *Petunia×hybrida* seedling selection, not patented.

Propagation:

*Type cutting.*—Vegetative cuttings.

*Time to initiate roots, summer.*—About 7 days at 25° C.

*Time to initiate roots, winter.*—About 10 days at 20° C.

*Time to develop roots, summer.*—About 15 days at 25° C.

*Time to develop roots, winter.*—About 21 days at 20° C.

*Root description.*—Fine, fibrous, whitish in color.

*Rooting habit.*—Freely branching; dense.

Plant description:

*Form.*—Annual flowering plant; indeterminate; initially upright, then low spreading and trailing. Vigorous growth habit. Freely basal branching with about seven main lateral branches per plant with lateral branches potentially forming at every node.

*Usage.*—Appropriate for hanging baskets, window boxes, patio containers and landscape applications.

*Plant height.*—About 7 cm.

*Plant diameter.*—About 28 cm.

*Lateral branches.*—Length: About 14 cm. Diameter: About 2 mm. Internode length: About 8 mm. Texture: Pubescent. Color: 144A.

*Foliage description.*—Arrangement, before flowering: Alternate, simple. Arrangement, when flowering: Opposite, simple. Length: About 4.5 cm. Width: About 2.3 cm. Shape: Elliptical. Apex: Acute. Base: Attenuate. Margin: Entire. Texture, upper and lower surfaces: Glandular, viscid; pubescent. Venation pattern: Pinnate, arcuate. Color: Developing foliage, upper surfaces: 143A. Developing foliage, lower surface: 146B. Fully expanded foliage, upper surface: Darker than 146B. Fully expanded foliage, lower surface: 146B. Venation, upper and lower surfaces: 144A. Petiole length: About 1 cm. Petiole diameter: About 2 mm. Petiole texture, upper and lower surfaces: Sparsely pubescent. Petiole color, upper and lower surfaces: 146A.

Flower description:

*Flower type and habit.*—Small salverform flowers; flowers face upward or outward; single, axillary. Freely flowering, typically about five open flowers per lateral stem.

*Natural flowering season.*—Long day responsive; spring until frost in the autumn; flowering continuous during the flowering period.

*Flower longevity on the plant.*—About one week; flowers persistent.

*Fragrance.*—Faint; sweet, floral.

*Flower size.*—Diameter: About 3.5 cm. Tube length: About 3 cm. Throat diameter, distal end: About 1 cm. Tube diameter, proximal end: About 3 mm.

*Flower buds.*—Length: About 2.5 cm. Diameter: About 6 mm. Shape: Elongated oblong with ruffled apices. Color: 145C.

*Corolla.*—Arrangement/appearance: Single whorl of five petals, fused into flared trumpet with distinct clefts between petal lobes. Petal length from throat: About 1.5 cm. Petal width: About 1.5 cm. Petal shape: Roughly fan-shaped to obovate. Petal apex: Acute. Petal margin: Entire. Petal texture: Smooth, satiny. Color: Petal, upper surface, when opening and fully opened: 155D. Petal, lower surface, when opening and fully opened: 155C. Flower throat (inside): 155A. Flower tube (outside): 155C. Venation, upper petal surface: 148B. Venation, lower petal surface: 145A. Venation, throat: 145C. Venation, tube: 145B.

*Sepals.*—Arrangement/appearance: Single whorl of five sepals fused at base, star-shaped. Length: About 1 cm. Width: About 4 mm. Shape: Ligulate. Apex: Broadly acute. Margin: Entire. Texture, upper and lower surfaces: Glandular, viscid. Color, upper and lower surfaces: 144A.

*Peduncles.*—Length: About 3.5 cm. Width: About 1.25 mm. Angle: About 45° to the stem. Strength: Strong. Texture: Pubescent. Color: 144A.

*Reproductive organs.*—Stamens: Quantity/arrangement: Five, adnate to corolla tube. Anther shape: Ovoid. Anther length: Less than 1 mm. Anther color: 158B. Pollen amount: Scarce. Pollen color: 158A. Pistils: Quantity: One. Pistil length: About 1.7 cm. Stigma shape: Anvil-shaped; rounded. Stigma color: 151B. Style length: About 1 cm. Style color: 145B. Ovary color: 144A.

*Fruit/seed.*—Fruit and seed production has not been observed.

Disease/pest resistance: Plants of the new *Petunia* have not been noted to be resistant to pathogens and pests common to *Petunia*.

Garden performance: Plants of the new *Petunia l have been observed to have good garden performance and to be tolerant to rain, wind and temperatures ranging from* −5 to 40° C.

It is claimed:

1. A new and distinct cultivar of *Petunia* plant named 'Bluette White', as illustrated and described.

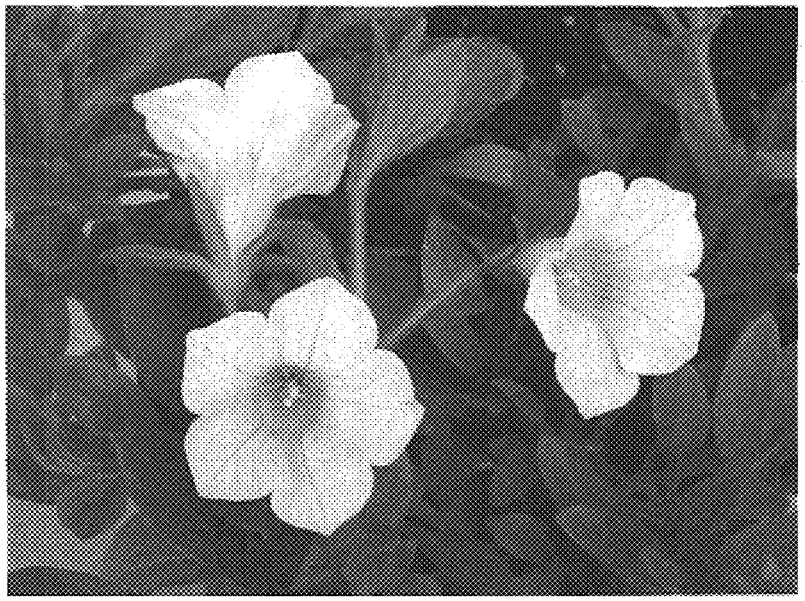
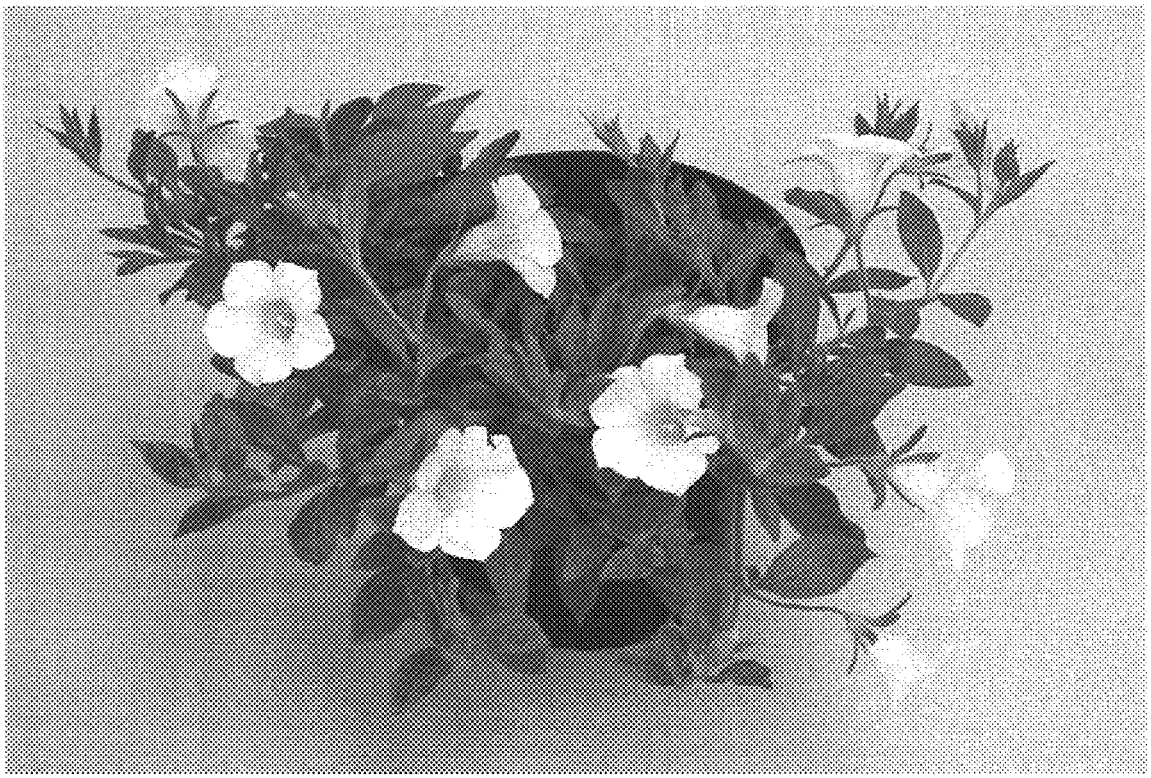

* * * * *